US011940400B1

(12) United States Patent
Bryan et al.

(10) Patent No.: US 11,940,400 B1
(45) Date of Patent: Mar. 26, 2024

(54) GAS SENSOR SYSTEMS AND METHODS OF USING SAME

(71) Applicant: Gas Activated Systems, The Woodlands, TX (US)

(72) Inventors: Michael A. Bryan, Spring, TX (US); Robert Bodnar, Edmond, OK (US); James Yu, Sugarland, TX (US)

(73) Assignee: Gas Activated Systems, The Woodlands, TX (US)

( * ) Notice: Subject to any disclaimer, the term of this patent is extended or adjusted under 35 U.S.C. 154(b) by 0 days.

(21) Appl. No.: 16/874,425

(22) Filed: May 14, 2020

Related U.S. Application Data

(60) Provisional application No. 62/848,454, filed on May 15, 2019.

(51) Int. Cl.
  *G01N 33/00* (2006.01)
  *G01N 9/00* (2006.01)
  *G01N 25/18* (2006.01)

(52) U.S. Cl.
  CPC ............... *G01N 25/18* (2013.01); *G01N 9/00* (2013.01); *G01N 33/0006* (2013.01); *G01N 33/0036* (2013.01)

(58) Field of Classification Search
  CPC .................................................... G01N 25/18
  USPC ......................................................... 73/25.03
  See application file for complete search history.

(56) References Cited

U.S. PATENT DOCUMENTS

| 9,739,739 | B2* | 8/2017 | De Coulon | G01N 27/18 |
| 2003/0039299 | A1* | 2/2003 | Horovitz | G01N 27/123 |
|  |  |  |  | 374/141 |
| 2016/0238494 | A1* | 8/2016 | Chrin, II | G01N 1/2273 |
| 2018/0052124 | A1* | 2/2018 | Rogers | G01N 29/326 |

FOREIGN PATENT DOCUMENTS

WO  WO-2018020057 A1 *  2/2018

OTHER PUBLICATIONS

Zhang et al. Translation of CN 208238837 U. Published Dec. 2018. Accessed Jun. 2022. (Year: 2018).*

* cited by examiner

*Primary Examiner* — Walter L Lindsay, Jr.
*Assistant Examiner* — Philip T Fadul

(57) ABSTRACT

A gas sensor system includes at least one gas sensor configured to receive at least one gas to be sampled; a processor configured to implement computer executable instructions; a first output interface in communication with the processor; and a computer memory in communication with the processor. A method includes measuring a density of the at least one gas; at least one of a) heating and b) cooling the at least one gas with a first thermal input; determining a first rate at which the at least one gas changes temperature when at least one of a) heating and b) cooling the at least one gas; comparing at least one of the density and the first rate to a reference database of gases; and determining at least one of a) a category b) a lower explosive limit and c) a concentration of the at least one gas.

20 Claims, 7 Drawing Sheets

GAS SENSOR SYSTEMS AND METHODS OF USING SAME

CROSS-REFERENCE TO RELATED APPLICATION(S)

This US non-provisional patent application claims the benefit and priority of U.S. Patent Application Ser. No. 62/848,454, titled "A GAS SENSOR SYSTEM AND METHODS OF USING SAME", filed on May 15, 2019, which is hereby incorporated by reference herein in its entirety, including all references and appendices cited therein, for all purposes.

FIELD

The disclosure relates generally to analysis instruments and sensors. The disclosure relates specifically to portable detectors of gases and, in some embodiments, combustible or explosive gases.

BRIEF DESCRIPTION OF THE DRAWINGS

In order that the manner in which the above-recited and other enhancements and objects of the disclosure are obtained, a more particular description of the disclosure briefly described above will be rendered by reference to specific embodiments thereof which are illustrated in the appended drawings. Understanding that these drawings depict only typical embodiments of the disclosure and are therefore not to be considered limiting of its scope. The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale.

DETAILED DESCRIPTION

Figure 1:
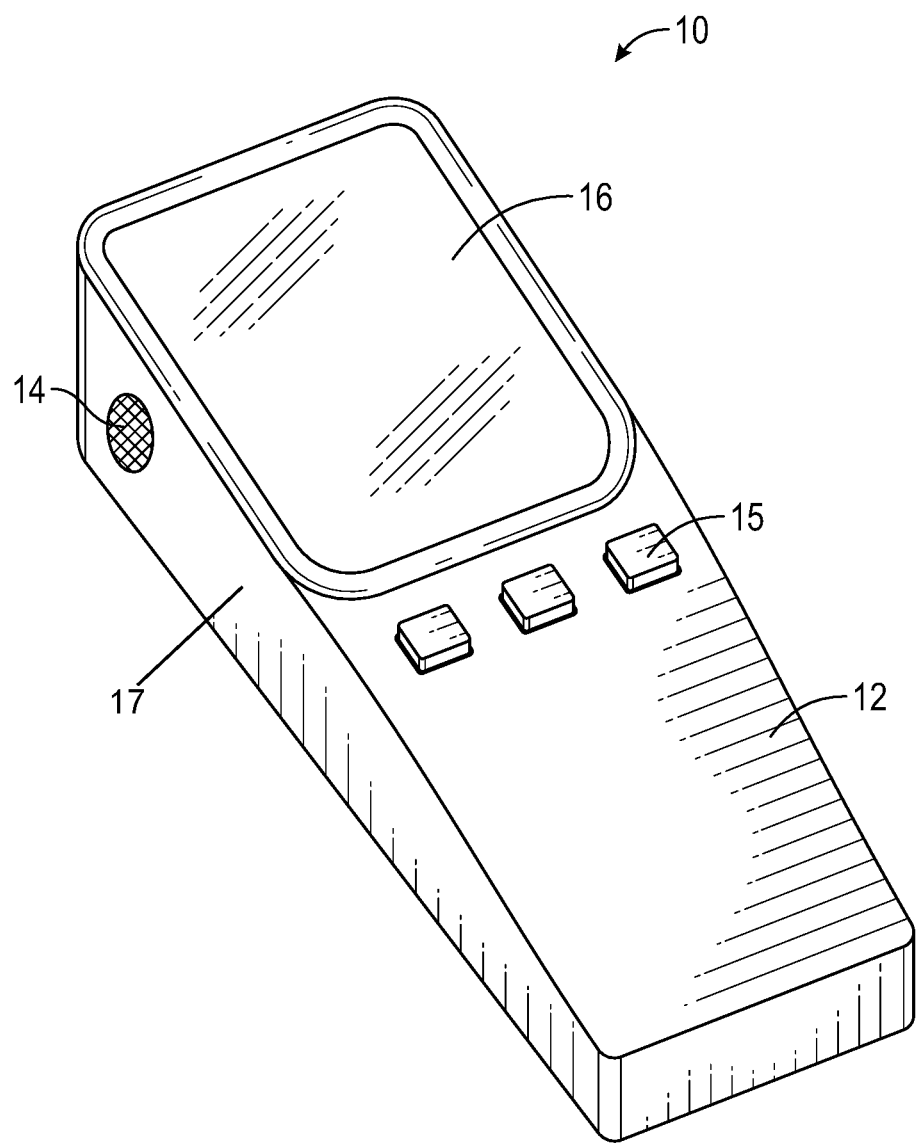
FIG. 1 is a perspective view of an embodiment of a gas sensor system incorporated into a handheld unit or handheld shell.

For context, fire and explosion are some of the most serious hazards associated with hydrocarbon production. During drilling, fracturing, completions and other oil well exploration production, transportation and refining processes, there may be instances in which hydrocarbon gas or vapor is released.

A gas leak may occur in any phase of currently operational oil and gas processes, at the transportation or refining stages, and at abandoned and orphaned oil wells. Leaks may be identified at pressure points in the systems, such as at plugs, seals, gaskets and valves. From pipelines through refineries to storage facilities, leaks may be detected and mitigated through a variety of technologies and methods. In some instances, oil and gas operations may present fugitive and vented emissions, such as methane ($CH_4$) emissions that come from any of oil and natural gas production, processing, transmission, and distribution—just to name a few. While fugitive gas typically may be primarily methane, it may also contain other heavier hydrocarbons such as ethane, propane, butane, acetone, as well as other hydrocarbon chemical compounds found at petrochemical plants.

Also, in areas like hydrocarbon tank farms and other areas where quantities of hydrocarbons liquids or gases are stored, often times stores with inadequate identifying marks and with multiple species in one location, it is desirable to know what the lower explosive limit or LEL is, for the entire collection of chemicals present.

In addition, in public safety and first response, there are frequent opportunities to encounter combustible and explosive gases of unknown composition in sites of burning factories, burning chemical trucks, terrorist attack and the like.

Therefore, it has been recognized that it is desirable to detect both systematic and random leaks in the oil and gas industry, in chemical industries, other industrial processes, and in situations where first responders find themselves at a scene in which potentially explosive and/or inflammable materials are present. Further, it has been recognized that it is desirable to detect such leaks with a device that can evaluate both single species as well as mixed gases of unknown species. Due to the explosive nature of hydrocarbon gases at certain concentrations, it is necessary to locate and repair leaks to prevent accidents and to keep operations at their optimum and to evaluate explosive gases.

Conventionally, various types of combustible gas sensors are utilized throughout many industries in the largely manual detection of gases. Technologies utilized may include electrochemical, photoionization, metal oxide semiconductor, catalytic, infrared, and laser—just to name a few.

Gas sensors may be ruggedized so as to survive harsh environments. Gas sensors may be dropped, exposed to extreme temperatures, humidity, moisture, dust, mud, and sludge as well as simple harsh mechanical treatment. Any of these variables and environmental conditions may factor into a gas sensor's performance. Any filters that may be used in the sensor can become clogged from moisture, soot or dust. Enough mud or sludge may completely block the flow or reception of a gas to be detected from the sensor. Conventional sensors typically suffer from drift and may fail to hold a calibration. Because of these factors, calibration or bump testing of gas sensor typically is required for conventional sensors before using the sensor each day.

A bump test may provide an indication that the gas sensor is working properly and may help ensure continued calibration, especially in mission critical situations. The bump test checks that the sensor responds to a target gas and also verifies that the display presents an indication of the gas detected. The bump test typically confirms that all the alarms on the gas sensor are activated. Because of the broad range of gas sensor applications, many different ways to perform bump tests have been adopted. A conventional bump test includes exposing a gas sensor to a known concentration of a target gas and obtaining a reading. The reading may be compared to the actual quantity of gas present, and if the sensor triggers an alarm within an acceptable range of the actual concentration, usually within a range of plus-or-minus ten percent of the known concentration of the gas, then the sensor is presumed to be working safely. If the bump test results are not within the acceptable range, or the sensor takes more than a prescribed amount of time to indicate the presence of the gas and/or indicate an alarm, the gas sensor must not be used until a full calibration has been conducted.

Gas sensors are subject to changes in gas sensitivities for each new species which will result in a new calibration requirement for each species. There is also calibration drift that may occur as a normal function of the chemical response change of a sensor. Calibration drift may occur over time because of chemical degradation of sensors and/or the natural drift in electronic components. Sensors may be exposed to environmental conditions that can affect their performances, such as temperature, humidity, airborne particles and vapors, sensor poisons and inhibitors, and high concentrations of target gases. The sensor also may be dropped on hard surfaces or in water or handled often enough so that vibrations may affect electronic components. For example, catalytic bead sensors that are used for detecting combustible gases may lose sensitivity in part or possibly completely after exposure to compounds such as silicones, which may form a coating on the catalyst and thereby block or inhibit the requisite gas reactions necessary to detect a target gas. The use of a defective and/or a low sensitivity sensor may increase potential risks as the sensor may provide a false positive or a false negative reading and/or otherwise potentially inaccurate reading. Therefore, the gas sensors may require calibration to improve and/or ensure the accuracy of the sensor.

A detector of the present disclosure can be used in a dynamic environment where the multiple gas species and concentrations may evolve from a light hydrocarbon, such as methane to some heavy gas, such as xylene vapor. In that case, a conventional detector, using a catalytic bead sensor, would under-report the concentration and a worker would be in a dangerous situation. The detector continues to show some non-zero LEL but catalytic beads under report, by a large amount, heavier explosive gases.

In addition, a detector that can be configured to communicate with other detectors and in the event that a single detector cannot electronically connect to the gateway, by connecting with another nearby detector, the ability for the mesh network to shuttle or pass data that may have gone directly from one detector to a gateway, now from one detector that cannot electronically connect to the gateway, to another detector than can connect to the gateway, shuttling or linking with a full mesh network and getting the information to the gateway by shuttling or round robin type of data passing. When a fleet or field of devices is deployed and the connection to the gateway is facilitated using a LoRA (Long Range) communication protocol, line of sight can be interrupted for some devices. By using a mesh network topology each detector can connect to a gateway or can transmit the data of other non-connected devices. Devices of the present disclosure can be implemented in a schema is in place to recognize communication disruption, and for the other devices to compensate for this disruption by shuttling the missing handhelds information back to the gateway. Or for instance some devices are inside a building with interrupted line of sight. Devices located at a doorway can sense both the inside of the building and the gateway and pass data.

In yet another advantage, the devices of the present disclosure may be utilized with little or no calibration. To be sure, calibration is frequently a challenging and time-consuming process and is typically a two-step procedure. In the first step, the instrument or sensor may be zeroed in fresh air, synthetic air, zero air, or a nitrogen background. This procedure allows the sensor to provide an indication or reading that is equal to the reading expected in clean air within the limits of the accuracy of the sensor (i.e., usually within 5% to 10% of the expected reading) and in this case would be a zero reading, or no combustible or flammable material present. The second step of the calibration process is to expose the sensor to a calibration gas that contains a known concentration of a gas that the sensor is designed to detect and/or measure. After exposing the sensor to the calibration gas a user may adjust the sensor to the correct reading to account for any deviation in the indication or reading of the calibration gas provided by the sensor. An example calibration gas may include 50% methane in air.

Limitations with many conventional detectors typically include the need to calibrate frequently to a specific gas standard and the need to enter manually various correction (s) to measure species of gas different than the calibration gas. In addition, these gas sensors may have to be manually adjusted or corrected to handle the measurement of two more species at once. In addition, advanced knowledge of the anticipated concentration of both species is needed. If the species and the concentration of multiple gases is not known in advance, conventional sensors may not be able to obtain an accurate measurement, at least because the user may not be able to enter the proper calibration factors. Further, the user may not accurately perform calculations necessary to derive the combined calibration factor.

In view of the above, it is the objective of the present disclosure to provide a portable, easy to use, economical, reliable, and accurate gas sensor which does not require bump testing and calibration and that can be used to detect accurately the lower explosive limit (LEL) of any number of individual or combined explosive gases.

Conventionally, various types of combustible gas sensors are utilized throughout the oil and gas industry. These devices are typically used in the manual detection of singular gases. These sensors only detect a single species of gas. Therefore, in order to detect different combustible gases and vapors such as methane, ethane, propane, butane and acetone, different kinds of gas sensors may be employed to detect different kinds of gas. The use of multiple and different sensors may increase the cost and complexity of the gas detection system. Additionally, conventional gas sensors do not detect others or significantly under-report other gases.

An embodiment of a gas sensor of the present disclosure comprises a plurality of probes in a micro-electromechanical system, or MEMS array, and each of the probes detects at least one quality or at least one parameter of a gas to be detected. The gas sensor optionally includes a memory to store at least one or more data points, such as reaction data of at least one of the plurality of probes as calculated when a given probe or at least one of the plurality of probes is exposed to at least one or more gases to be detected in at least one or more different concentrations.

The gas sensor optionally does not require bump testing and/or calibration. An example gas sensor of the present disclosure may detect any one or more of a lower explosive limit (LEL) of at least one species of gas and/or a lower explosive limit of a plurality of explosive gases. For example, at least two or more explosive gases can be sensed by the gas sensor. The gas sensor may detect a lower explosive limit of any number of mixed gases and/or any concentration of each of a plurality of gases. The gas detector may detect a single explosive gas or a combination of a plurality of gases even if the type of gas or gases, the concentration of the gas or gases, and the combination of gases is unknown prior to detection. The gas sensor may be configured to detect an aggregate LEL for the combination of gases.

An embodiment of a handheld detector comprises a gas sensor. The handheld detector optionally includes a wireless or wired communication ability with at least one of another detector or detectors, a computer, a tablet, a cell phone or smart phone, other electronics, the Internet, or a cloud computing environment. The gas sensor can be configured to communicate with a gateway or wireless access point, either directly or through mesh or networked communication with other sensors (which may include similarly or differently configured gas sensors).

The handheld detector optionally includes an output to receive an indication of a data recorded by the gas sensor, which may include a display screen. The output may display any one or more of a) a type or identification of the at least one detected gas, b) a concentration of the at least one detected gas, and c) a lower explosive limit (LEL) of the at least one gas. Optionally, the display may provide an indication of any of the data disclosed herein for a combination or a plurality of gases.

The handheld detector may include a display showing at least one aggregate or combined lower explosive limit of a plurality of gases. Optionally, the handheld detector may wirelessly communicate with at least one other handheld detector. The hand-held detector may include a global positioning system (GPS) receiver or chip or other positioning system (e.g., cell-tower triangulation with a cell tower receiver).

The handheld detector may communicate with at least one other detector, which may including receiving and/or transmitting data to the at least one other detector, and may display at least an indication of any data, such as a type of at least one gas, a concentration of at least one gas, and a lower explosive limit of at least one gas detected by the at least one other detector, and thereby provide a user with an indication of at least one of the type of at least one gas, the concentration of at least one gas, and the lower explosive limit of at least one gas in dispersed area detectable by the handheld detector and the at least one other detector.

A method of using a handheld detector may include deploying at least a first gas detector on at least one side of a fire or explosion barrier. The method further may include communicating with the at least a first detector with a handheld gas detector. The handheld detector may receive at least one of a data and an indication of at least one of the type of at least one gas, the concentration of at least one gas, and the lower explosive limit of at least one gas in dispersed area detectable by the at least a first detector and display at least one gas, the concentration of at least one gas, and the lower explosive limit of at least one gas in dispersed area detectable by the at least a first detector at the handheld gas detector.

In some embodiments, the present invention pertains to a gas detector that may include a micro electro-mechanical system, or MEMS, based silicon gas detectors that optionally may be incorporated onto a printed circuit board, or PCB. The gas detector or gas system may detect accurately any explosive or combustible gas from a fraction of a lower explosive limit, or LEL, to 100% LEL. The gas detector may detect at least one and, optionally, a plurality of gases, without a user having prior knowledge of the type and/or the concentration of the gas or gases to be detected. The gas detector may provide an indication, optionally through an output, to the user of at least one of a) a type or identification of at least one detected gas, b) a concentration of the at least one detected gas, and c) a lower explosive limit (LEL) of the at least one gas. Optionally, the display may provide an indication of any of the forgoing data for a combination or a plurality of gases. The output can be coupled with a display or could include a wireless or wired interface for transmitting the aforementioned data to a remote display or to a connected system.

It will be understood that when a sample undergoes a physical transformation, such as any type of phase transition, more or less heat will need to flow to it compared to the reference to maintain both at the same temperature. Whether less or more heat is needed to flow to the sample depends on whether the transformation process is exothermic or endothermic. For example, in many cases, as a solid sample melts to a liquid, the sample may require more heat flowing to the sample to increase its temperature at the same rate as the reference. This is due to the absorption of heat by the sample as it undergoes an endothermic phase transition from solid to liquid. Likewise, as the sample undergoes an exothermic process (such as crystallization), less heat may be required to raise the sample temperature. By observing the difference in heat flow between the sample and reference, differential scanning calorimeters are able to measure the amount of heat absorbed or released during such transition.

An example gas sensor of the present disclosure may include a MEMS micro-hotplate structure, which may be one or both of two types. A first type includes a closed-type membrane micro-hotplate includes a membrane that overlaps a silicon substrate along its periphery. The second type includes a suspended-type membrane, where the membrane is supported on the silicon substrate by means of supporting beams. In both cases, the membrane lies over a cavity etched in the silicon substrate. In the latter case, the thermal losses to the substrate take place only through the supporting beams, and thus they are minimized compared to the closed-type membrane. The disclosed gas sensor systems may use either the closed-membrane or suspended-membrane micro-hotplate. For example, if a plurality of gases, including potentially dozens or even hundreds of gases, were present in an area, the gas detector would correctly display at least one of a) a category and, optionally, a type or identification of at least one detected gas, b) a concentration of the at least one detected gas, and c) a lower explosive limit (LEL) of the at least one gas and, optionally, the display may provide an indication of any of the forgoing data for a combination or a plurality of gases, including an aggregate LEL. Also, a user would not be required to have in-advance knowledge of the gas under measurement nor would calibration of the gas detector for the unknown gas or gases be required because the gas detector would be able to detect accurately the gas or gases without such a calibration.

In some embodiments, the sensor can be incorporated into a fixed detector or handheld detector which optionally includes a display screen that shows at least one of a) a lower explosive limit, b) an aggregate or combined lower explosive limit for at least one gas or a plurality of gases, and c) a concentration for at least one gas and/or a concentration for each of a plurality of gases or a concentration of the plurality of gases in combination. The detector can have a display showing at least one aggregate lower explosive limit of all the combined explosive gases.

In some embodiments, the detector optionally includes wireless or wired communication interface with at least one another detector or detectors, a computer, a tablet, a cell phone or smart phone. The communication can be Bluetooth, Wi-Fi, LoRA, ZigBee or others. Therefore, the detector may wirelessly communicate with other fixed and/or handheld detectors. The handheld detector may include a global positioning system (GPS) receiver or chip or other positioning system (e.g., cell-tower triangulation with a cell tower receiver). The handheld detector may communicate with at least one other detector, which may including receiving and/or transmitting data to the at least one other detector, and may display at least an indication of any data, such as a type of the at least one gas, a concentration of the at least one gas, and a lower explosive limit of the at least one gas detected by the at least one other detector, and thereby provide a user with an indication of at least one of the type of the at least one gas, the concentration of the at least one gas, and the lower explosive limit of the at least one gas in dispersed area detectable by the handheld detector and the at least one other detector. In addition, the sensor may communicate with a gateway device or for instance a LoRA concentrator that can receive signals from a plurality of sensors and can in a preferred embodiment aggregate the information both locally for user display and interpretation and also send by radio, LTE or other suitable method, for use, display and potentially future processing in the cloud. In some embodiments, the sensor optionally may not require at least one of a) bump testing and b) calibration. Optionally, the sensor may not require a correction factor to be entered to detect at least one type of gas that is different than the type of gas the sensor is otherwise configured to and/or calibrated to detect.

A plurality of the sensors may be used in a gas detection system to monitor and quantify gas emissions at oil and gas exploration and production sites, refineries, storage, and transmission facilities. Through this system, gas emissions may be monitored, mapped, and analyzed in real-time, providing the intelligence necessary for immediate remediation of methane and other combustible emission sources. A system and method of using a handheld detector may include deploying at least a first gas detector on at least one side of a fire or explosion barrier. The method further may include communicating with the at least a first detector with a handheld gas detector. The handheld detector may receive at least one of a data and an indication of at least one of the type of the at least one gas, the concentration of the at least one gas, and the lower explosive limit of the at least one gas detectable by the at least a first detector and display at the handheld gas detector at least one of the type of gas, the concentration of the at least one gas, and the lower explosive limit of the at least one gas detectable by the at least a first detector.

Figure 2:
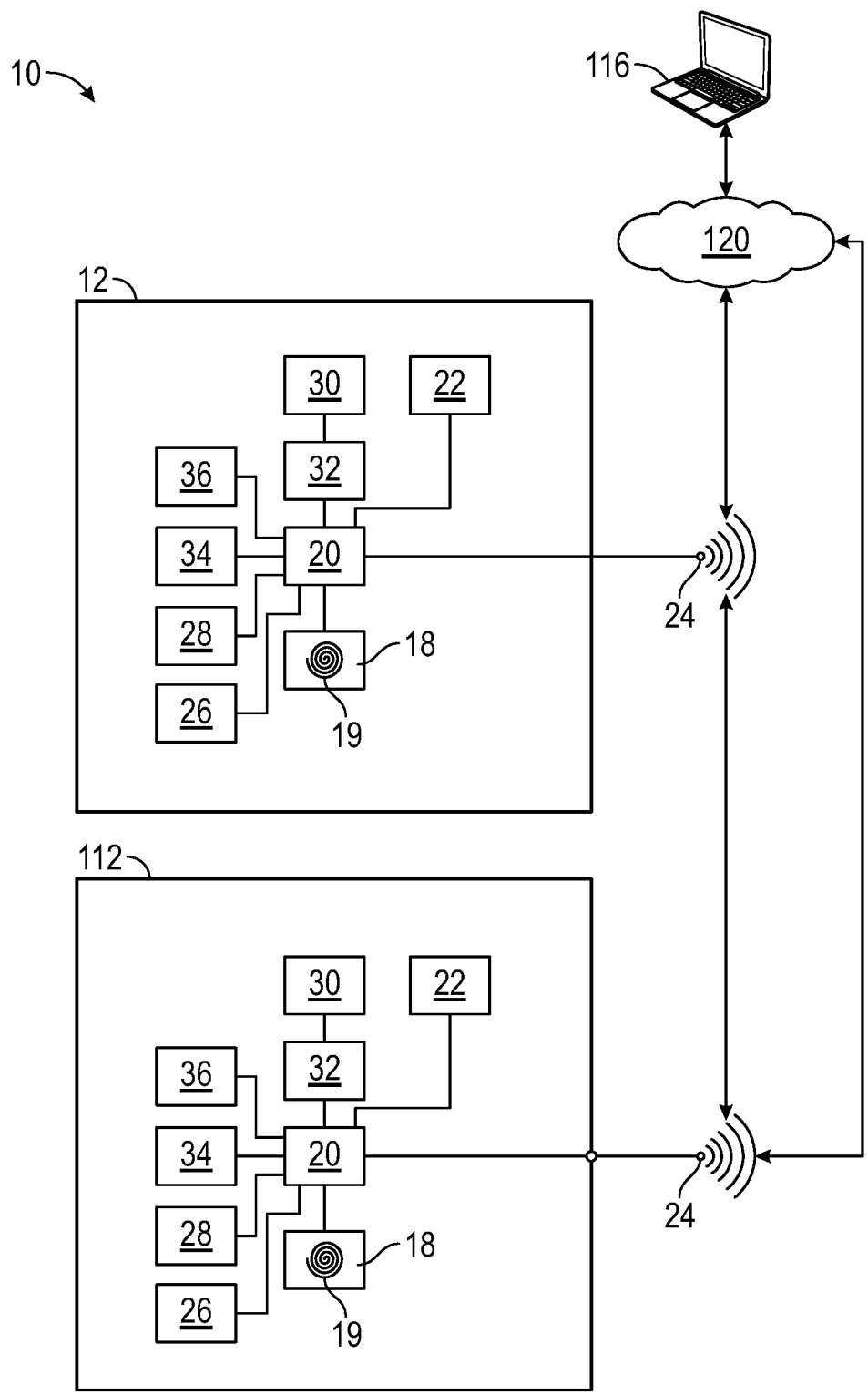
FIG. 2 is a schematic representation of a gas sensor system incorporated into a handheld unit and a node in wireless communication with each other and remote computer systems.

Referring to FIGS. 1 and 2, a gas sensor system 10 may optionally be incorporated into a handheld unit or shell, a node 112 (FIG. 2) for remote placement, such as near potential sources of gases or on an exposed or at-risk side of a safety barrier. The handheld unit 12 or node 112 may include a port 14, opening, or aperture through which at least one gas to be tested can pass. Optionally, a fan (not illustrated) may be positioned within a housing 17 of the handheld unit 12 to draw the at least one gas through the port 14 or the gas may pass passively into the port 14.

The handheld unit 12 may optionally include at least one or a first output interface 16, and while the node 112 typically does not include an at least one or a first output interface 16, it too may optionally include the output interface 16. The output interface 16 is configured to display data perceivable to the user such as a) a category and, optionally, an identification of the at least one gas b) a lower explosive limit and c) a concentration of the at least one gas on at least the first output interface. The category may be a function of a number of carbon atoms present in the at least one gas. For example, the sensor (as explained below) may determine that the at least one gas includes one carbon atom, which may include gases like methane and other light gases. Heavier gases (depending on temperature of course), may include benzene with six carbon atoms. Consequently, the gas sensor may be able to identify broad categories of gases (no carbon, e.g., hydrogen; light; medium; and heavy and categorize the detected gas or gases in "bins" of 0, 1-2, 2-3, 3-7, 7+ carbon atoms). The categories set forth above are not intended to be limiting, but are merely examples. The categories could be identified as small, medium, and large, based on relative chemical or molecular weights/sizes, as an example. The exact boundaries or ranges of what falls within each of these categories may depend on particularities of chemical(s) being sensed. Also, the delineation of categories can be based on other gas properties rather than weights/sizes. The categories may be fewer or more bins that the examples provided herein.

Based on this information a user may be able to determine a source or likely source of the gas. For example, a user may make operational real-time (or near-real-time) decisions depending on whether methane at an oil well (a conventional gas released sometimes uncontrollably that would suggest action at low concentrations (bin 2)), for example, versus a gas that is detected and categorize in bin 4 or 5, which would not usually be encountered from drilling operations and suggests a spilled solvent container that may pose a less emergent danger.

The gas sensor system 10 may include at least one gas sensor 18 configured to receive at least one gas to be sampled. Optionally, the at least one gas sensor is a microelectrical mechanical system, which in turn may optionally be at least one micro-hotplate 19. The micro-hotplate 19 optionally may be a closed-membrane micro-hotplate or a suspended membrane micro-hotplate. The gas sensor 18 may comprise a plurality of gas sensors, where at least one gas sensor measures the at least one gas and at least a second gas sensor measures a reference gas.

The gas sensor system 10 optionally includes a processor 20 configured to implement computer executable instructions stored in memory. It will be understood that examples discussing processes executed by the gas sensor system 10 include the execution of instructions by the processor 20.

The gas sensor 10 also may include at least one or a first output interface 16 as mentioned above. Optionally, the output interface 16 is integrated into the handheld unit 12. The output interface 16 may optionally display data generated from at least one node 112. The output interface 16 may also include a remote computer(s) and display or remote output interface 116 that is coupled, whether wirelessly or wired, directly to the handheld unit 12, node 112, or via the cloud or Internet 120. Optionally, the output interface 16 may display data collated and transmitted via the remote computer 116. In other words, the remote computer 116 may be linked to multiple handheld units 12 and/or nodes 112 and transmit individual or collated data from any one or more of the handheld units 12 and/or nodes 112 to a given handheld unit. Alternatively, the remote computer 116 may display on the remote display data from multiple handheld units 12 and/or nodes 112.

The gas sensor system 10 may include at least one of a) wireless communication component and b) a wired communication component 24 coupled to the processor 20 such that the handheld unit 12, node 112, and remote computer 116 may communicate with each of the others. The wireless component may be any type of wireless communication equipment and/or standard known or developed, such as Bluetooth, Wi-Fi, LoRA, and the like, or hardwired such as by Ethernet cable.

Optionally, the gas sensor system 10 may include at least one input interface 15, which may include a touchscreen, buttons, and the like to allow a user to turn the gas sensor system 10 one and off, implement various commands, menus, functions, and the like.

The gas sensor system 10 also may include at least one of a positioning system 26, such as a global positioning system receiver, an accelerometer 28, and a power supply 30, such as an AC (alternating current) or DC (direct current), such as batteries, power supply with an optional charging circuit 32, a humidity sensor 34, and a pressure sensor 36. Each of the positioning system 26, accelerometer 28, and power supply 30, may be coupled to the processor 20. Data from the accelerometer 28 may be used by a computer executable instruction implemented by the processor 20 to implement a shock-proofing protocol in the even the gas sensor system 10 undergoes a fall or rapid shock, or it may implement an alarm or alert status to be transmitted to the remote computer 116 in the event no movement is detected over a set period of time, which may suggest that the user has succumbed to an environmental hazard.

The gas sensor system 10 may also include a computer memory 22 in communication with the processor 20. The computer memory 22 is configured to store data representing a reference database of gases, both individually and optionally in various combinations. The reference data may include one or more rates at which known gases and known combinations of gases increase and/or decrease temperature when exposed to a first thermal input of known intensity; density; molar weights; phase transition temperatures; and other physical constants and data derived from calculation or empirically before testing the at least one gas.

The computer memory 22 also may be configured store computer executable instructions, that when implemented by the processor 20 cause the processor 20 to perform functions comprising: measuring a density of the at least one gas; at least one of a) heating and b) cooling the at least one gas with a first thermal input; determining a first rate at which the at least one gas changes temperature when at least one of a) heating and b) cooling the at least one gas with the gas sensor 18; comparing at least one of the density and the first rate to a reference database of gases; determining at least one of a) a category b) a lower explosive limit and c) a concentration of the at least one gas; generating at least one output signal reflective of at least one of a) a category b) a lower explosive limit and c) a concentration of the at least one gas; and, displaying at least one of a) a category b) a lower explosive limit and c) a concentration of the at least one gas on at least the first output interface. Optionally, the functions further comprise both heating and cooling the at least one gas, wherein the first rate at which the at least one gas changes temperature is calculated when heating the at least one gas, and a second rate at which the at least one gas changes temperatures is calculating when cooling the gas; and comparing the second rate to the reference database.

Figure 4:
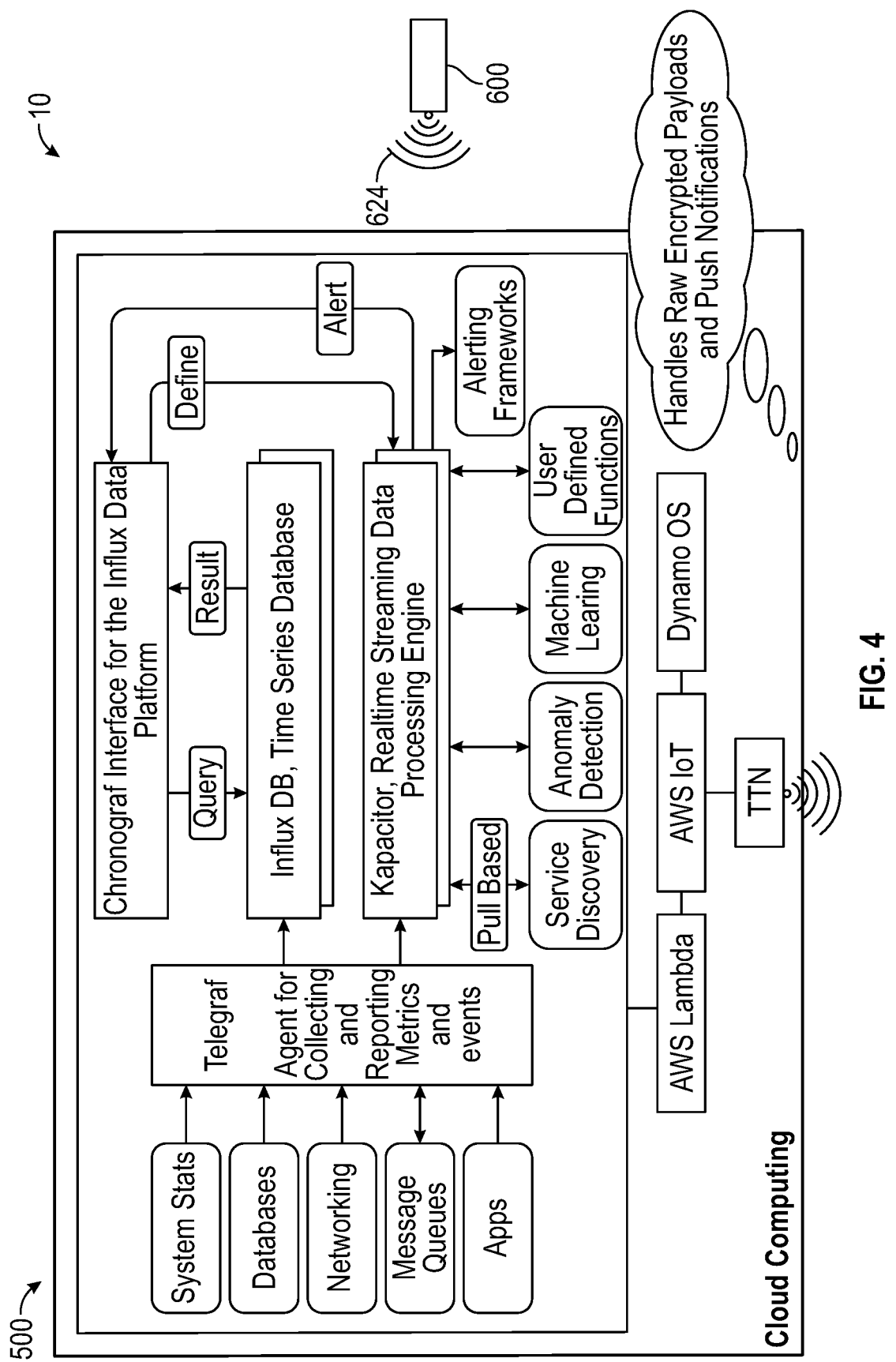
FIG. 4 is a schematic representation of a gas sensor system incorporated into a handheld unit and a node in wireless communication with each other, a gateway intermediary, and remote computer systems.
Figure 4:
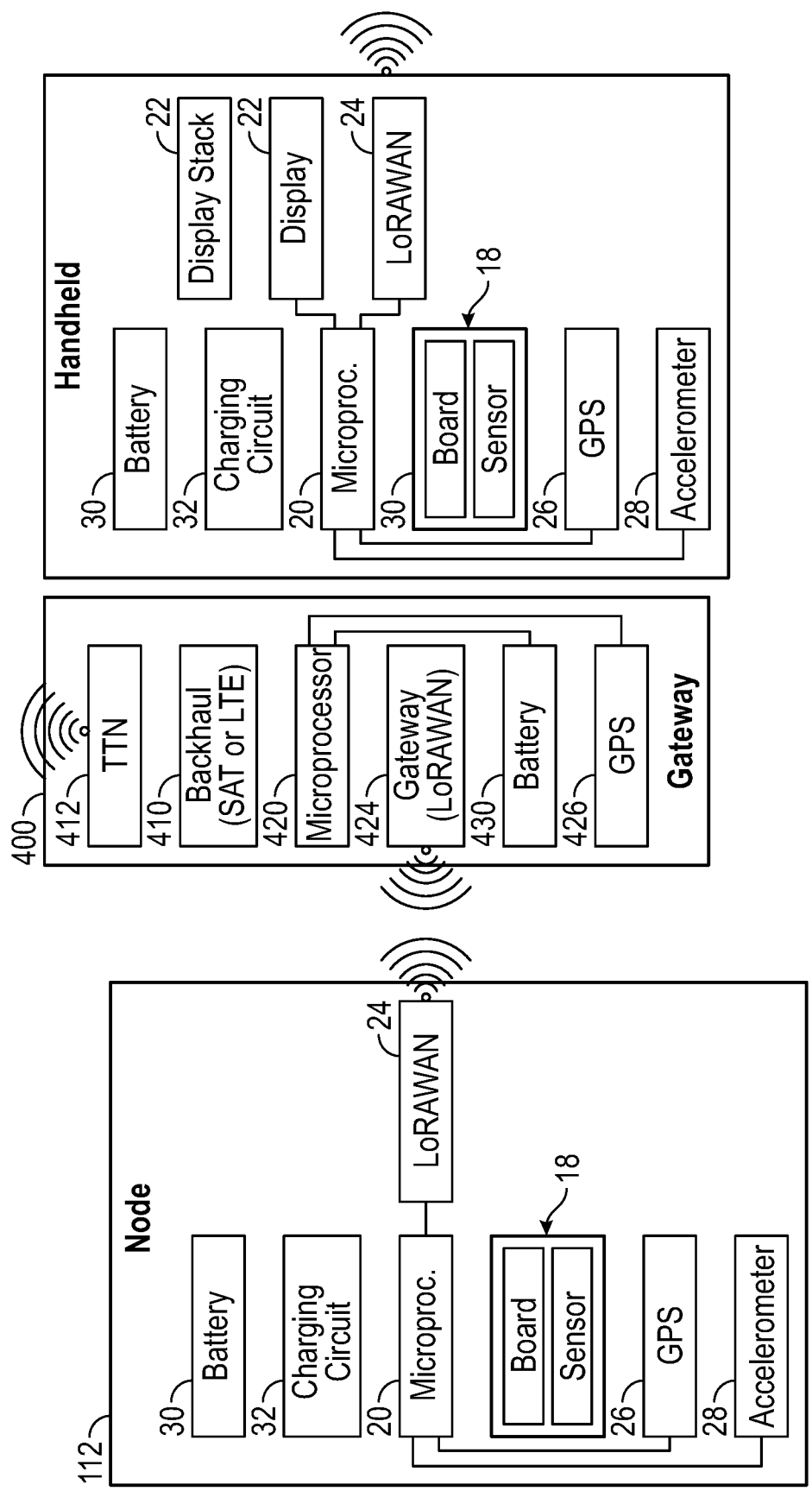
Figure 5:
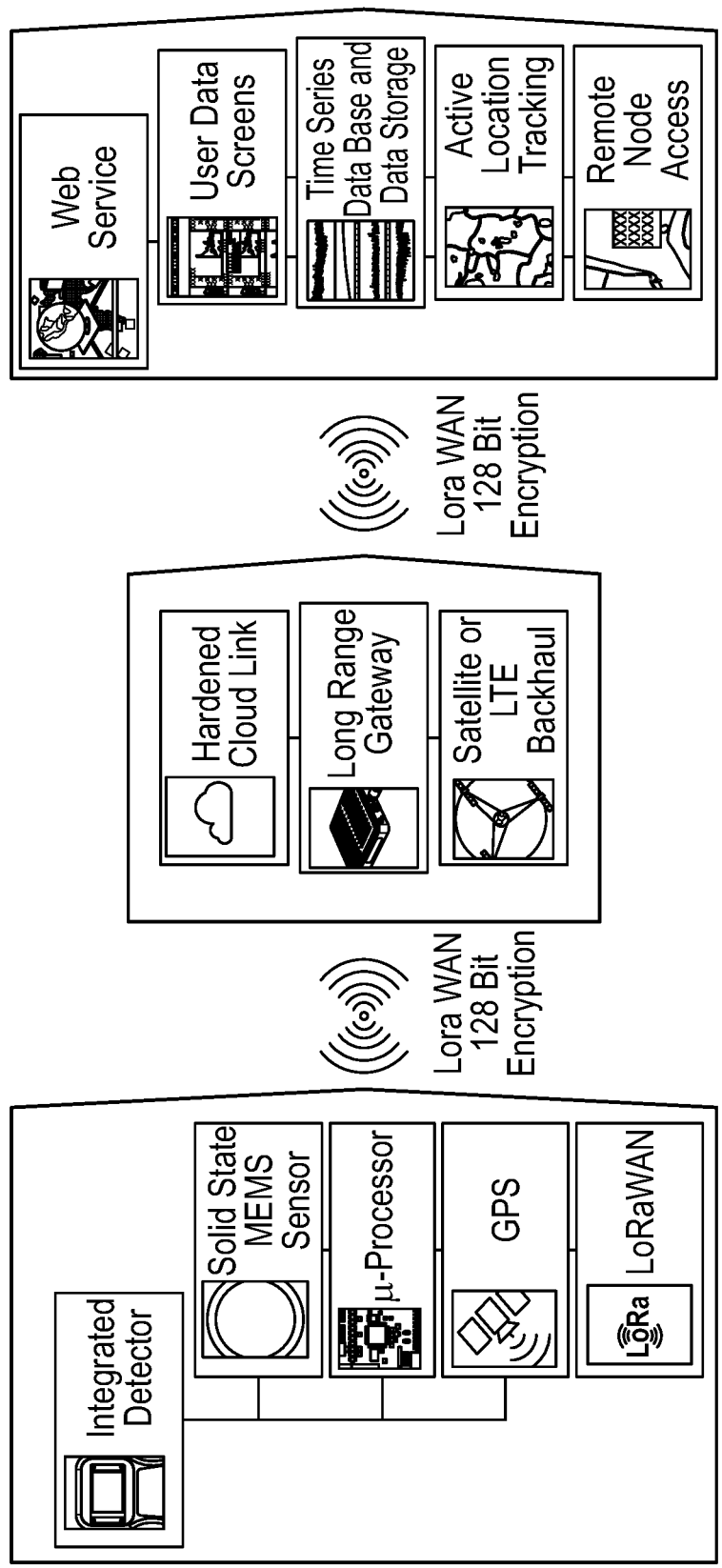
FIG. 5 is a schematic representation of a gas sensor system incorporated into a handheld unit and a node in wireless communication with each other, a gateway intermediary, and remote computer systems.
Figure 6:
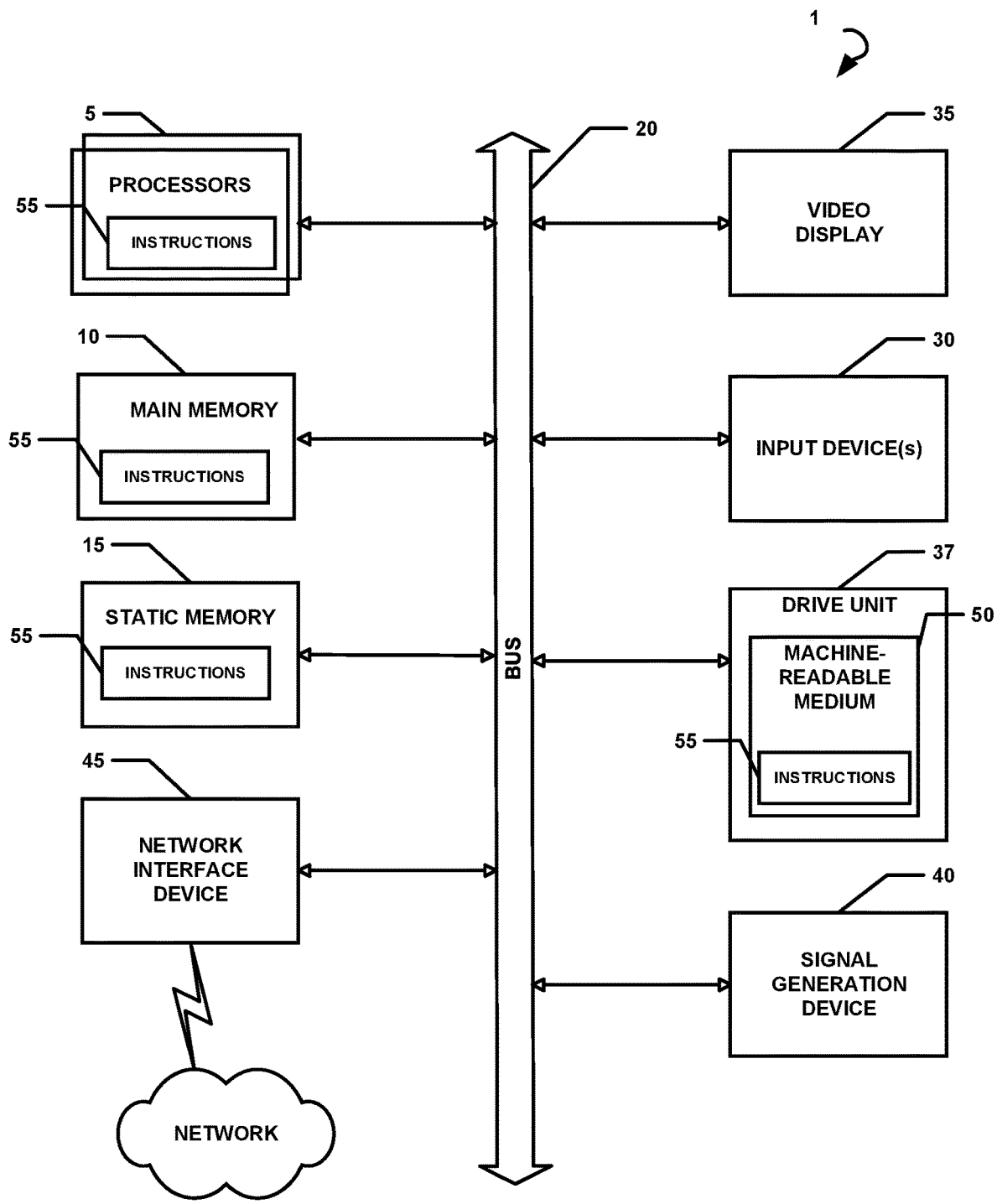
FIG. 6 is a schematic diagram of an example computer system that is used to implement embodiments according to the present technology

Optionally, and as disclosed in FIGS. 4 and 5, the gas sensor system 10 may include a gateway 400 configured to at least one of receive, collate, process, and redistribute data received from at least one of a handheld unit 12 and/or a node 112, or a plurality of one or both of these units/nodes. The gateway 400 optionally includes a processor 420 coupled to least one of a) wireless communication component and b) a wired communication component 424 such that the handheld unit 12, node 112, and remote computer 116 may communicate with each of the others. The wireless component may be any type of wireless communication equipment and/or standard known or developed, such as Bluetooth, Wi-Fi, LoRA, and the like, or hardwired such as by Ethernet cable. The gateway also optionally includes one or more of the following components that are similar to those described above: a power source 430, a charging circuit (not illustrated, but akin to the charging circuit 32 described above), a positioning system 426. The gateway 400 may include a backhaul system 410 coupled to the processor 420.

The backhaul system 410 may include at least one receiver and/or transmitter to connect the gateway 400 to a broader network, such as the Internet or a cloud. The backhaul system 410 may include a satellite and/or wireless (e.g., LTE, 5G, and the like) transmitters and/or receivers. The backhaul system 410 and/or the processor 420 may each be coupled directly or indirectly to a technology transfer node 412. The gateway 400, optionally through the technology transfer node 412, may encrypt and/or decrypt data transmitted from and received by the gateway 400, respectively, and bundle data into secure packets for transmission.

Turning to FIG. 5, the gas sensor system optionally includes a cloud platform 500 that is remotely accessed via the cloud or Internet 120 (FIG. 2). The cloud platform 500 includes one or more of the following apps and functions: authentication, time series data base in which data from the handheld unit(s) 12 and/or node(s) 112 and other potential sources is recorded, trend and feature extraction, dynamic display with recorded and/or real time information (such as from the time series database), and location and notification when selected events occur or data alarms are triggered. The cloud platform 500 may be accessed remotely, such as from a computer and display 116 (FIG. 2), a smart phone, terminal, and other such devices.

The gateway 400 and/or the cloud platform 500 may be coupled directly or wirelessly (e.g., by wireless component 624 identical to the wireless component 24 discussed above) to one or more components, such as valves and other equipment 600 that may be opened and/or closed in response to an actuation signal generated via an application or a module of the cloud platform 500 in response to data received from one or more handheld unit(s) 12, node(s) 112, or other sources of data. For example, the gas sensor 18 at a handheld unit 12 or node 112 may detect a potentially hazardous gas and transmits this data, either via the gateway 400 or directly to the cloud platform 500. The cloud platform 500, optionally via an app or a module, may trigger an actuation signal in response to the signal indicating the presence of the hazardous gas. The cloud platform 500 may then transmit the actuation signal to equipment 600, such as instructing the equipment 600 to close in the event it is a valve. Additionally or alternatively, the cloud platform 500 may transmit an actuation signal to the handheld unit 12 or a remote computer 116 (or smartphone or other such device), which in turn provides an observable indication for a user advising her of the proposed actuation signal and a recommendation to actuate the equipment 600.

Figure 3:
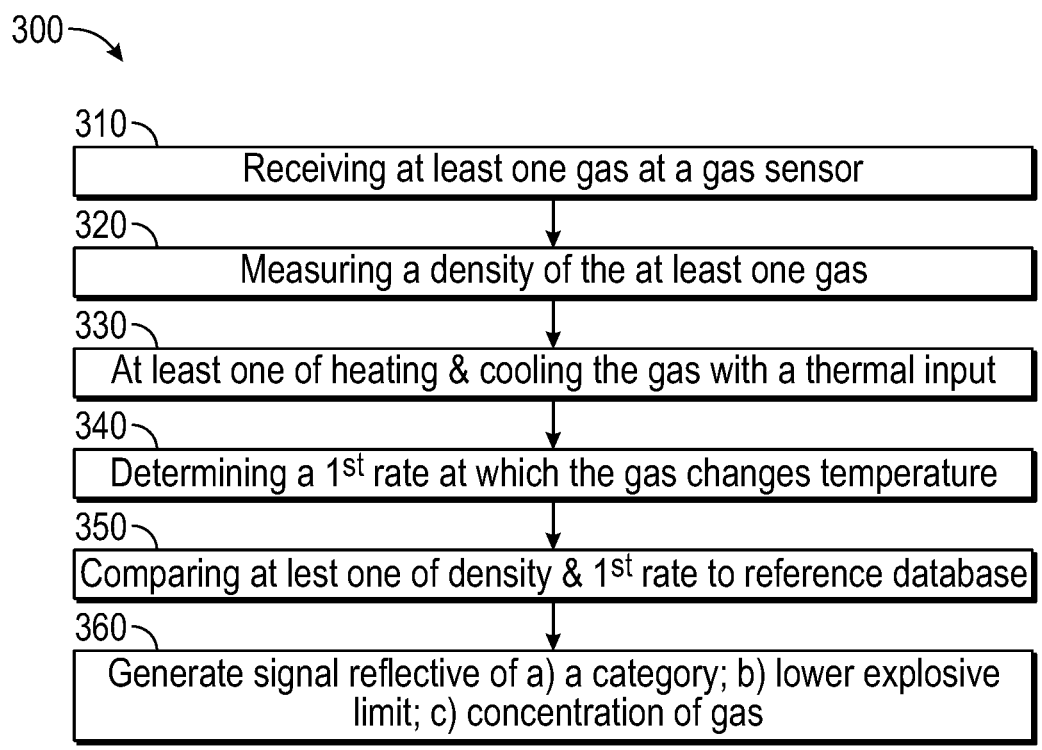
FIG. 3 is a flowchart of a method of determining at least one parameter of at least one gas.

With the gas sensor system 10 disclosed, a method 300 for detecting a parameter of at least one gas is explained in FIG. 3. The method includes step 310 of receiving the at least one gas at a gas sensor; step 320 of measuring a density of the at least one gas with the gas sensor 18; step 330 of at least one of a) heating and b) cooling the at least one gas with a first thermal input with the gas sensor 18; step 340 of determining a first rate at which the at least one gas changes temperature when at least one of a) heating and b) cooling the at least one gas; step 350 of comparing at least one of the density and the first rate to a reference database of gases; and step 360 of determining at least one of a) a category b) a lower explosive limit and c) a concentration of the at least one gas.

An example method may optionally include one or more of the steps of generating at least one output signal reflective of at least one of a) a category b) a lower explosive limit and c) a concentration of the at least one gas; displaying at least one of a) a category b) a lower explosive limit and c) a concentration of the at least one gas on at least a first output interface.

Optionally, the method may also include both heating and cooling the at least one gas, wherein the first rate at which the at least one gas changes temperature is calculated when heating the at least one gas, and a second rate at which the at least one gas changes temperatures is calculating when cooling the gas and comparing the second rate to the reference database. The heating and the cooling the at least one gas occurs sequentially using the at least one gas sensor and/or it may occur in parallel using a plurality of gas sensors. The method may further comprise calibrating the at least one gas sensor, although this typically is not necessary or required.

The method may include at least one of a) calculating a humidity of the at least one gas with, for example, the humidity sensor 34 and b) calculating the pressure of the at least one gas with, for example, the pressure sensor 36. The method may take one or both of the humidity data and the pressure data and compensate at least one of a) the density and b) the first rate for at least one of the humidity and the pressure.

The method may include identifying the at least one gas or the individual gases within a plurality of gases in the event a plurality of gases are received at the at least one gas sensor. Optionally, an aggregate lower explosion limit for the plurality of gases may be determined.

The method may further include wirelessly transmitting the at least one output signal reflective of at least one of a) a category b) a lower explosive limit and c) a concentration of the at least one gas to the at least the first output interface.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

FIG. 7 is a diagrammatic representation of an example machine in the form of a computer system 1, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a personal digital assistant (PDA), a cellular telephone, a portable music player (e.g., a portable hard drive audio device such as a Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The computer system 1 includes a processor or multiple processor(s) 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alphanumeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processor(s) 5 during execution thereof by the computer system 1. The main memory 10 and the processor(s) 5 may also constitute machine-readable media.

The instructions 55 may further be transmitted or received over a network via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

The components provided in the computer system 1 are those typically found in computer systems that may be suitable for use with embodiments of the present disclosure and are intended to represent a broad category of such computer components that are well known in the art. Thus, the computer system 1 can be a personal computer (PC), hand held computer system, telephone, mobile computer system, workstation, tablet, phablet, mobile phone, server, minicomputer, mainframe computer, wearable, or any other computer system. The computer may also include different bus configurations, networked platforms, multi-processor platforms, and the like. Various operating systems may be used including UNIX, LINUX, WINDOWS, MAC OS, PALM OS, QNX ANDROID, IOS, CHROME, TIZEN, and other suitable operating systems.

Some of the above-described functions may be composed of instructions that are stored on storage media (e.g., computer-readable medium). The instructions may be retrieved and executed by the processor. Some examples of storage media are memory devices, tapes, disks, and the like. The instructions are operational when executed by the processor to direct the processor to operate in accord with the technology. Those skilled in the art are familiar with instructions, processor(s), and storage media.

In some embodiments, the computer system 1 may be implemented as a cloud-based computing environment, such as a virtual machine operating within a computing cloud. In other embodiments, the computer system 1 may itself include a cloud-based computing environment, where the functionalities of the computer system 1 are executed in a distributed fashion. Thus, the computer system 1, when configured as a computing cloud, may include pluralities of computing devices in various forms, as will be described in greater detail below.

In general, a cloud-based computing environment is a resource that typically combines the computational power of a large grouping of processors (such as within web servers) and/or that combines the storage capacity of a large grouping of computer memories or storage devices. Systems that provide cloud-based resources may be utilized exclusively by their owners or such systems may be accessible to outside users who deploy applications within the computing infrastructure to obtain the benefit of large computational or storage resources.

The cloud is formed, for example, by a network of web servers that comprise a plurality of computing devices, such as the computer device 1, with each server (or at least a plurality thereof) providing processor and/or storage resources. These servers manage workloads provided by multiple users (e.g., cloud resource customers or other users). Typically, each user places workload demands upon the cloud that vary in real-time, sometimes dramatically. The nature and extent of these variations typically depends on the type of business associated with the user.

It is noteworthy that any hardware platform suitable for performing the processing described herein is suitable for use with the technology. The terms "computer-readable storage medium" and "computer-readable storage media" as used herein refer to any medium or media that participate in providing instructions to a CPU for execution. Such media can take many forms, including, but not limited to, non-volatile media, volatile media and transmission media. Non-volatile media include, for example, optical or magnetic disks, such as a fixed disk. Volatile media include dynamic memory, such as system RAM.

Transmission media include coaxial cables, copper wire and fiber optics, among others, including the wires that comprise one embodiment of a bus. Transmission media can also take the form of acoustic or light waves, such as those generated during radio frequency (RF) and infrared (IR) data communications. Common forms of computer-readable media include, for example, a floppy disk, a flexible disk, a hard disk, magnetic tape, any other magnetic medium, a CD-ROM disk, digital video disk (DVD), any other optical medium, any other physical medium with patterns of marks or holes, a RAM, a PROM, an EPROM, an EEPROM, a FLASHEPROM, any other memory chip or data exchange adapter, a carrier wave, or any other medium from which a computer can read.

Various forms of computer-readable media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU.

Computer program code for carrying out operations for aspects of the present technology may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The foregoing detailed description includes references to the accompanying drawings, which form a part of the detailed description. The drawings show illustrations in accordance with exemplary embodiments. These example embodiments, which are also referred to herein as "examples," are described in enough detail to enable those skilled in the art to practice the present subject matter. The embodiments can be combined, other embodiments can be utilized, or structural, logical, and electrical changes can be made without departing from the scope of what is claimed. The following detailed description is, therefore, not to be taken in a limiting sense, and the scope is defined by the appended claims and their equivalents.

In this document, the terms "a" or "an" are used, as is common in patent documents, to include one or more than one. In this document, the term "or" is used to refer to a nonexclusive "or," such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the invention in the form disclosed.

Many modifications and variations will be apparent to those of ordinary skill in the art without departing from the scope and spirit of the invention. Exemplary embodiments were chosen and described in order to best explain the principles of the present technology and its practical application, and to enable others of ordinary skill in the art to understand the invention for various embodiments with various modifications as are suited to the particular use contemplated.

While various embodiments have been described above, it should be understood that they have been presented by way of example only, and not limitation. The descriptions are not intended to limit the scope of the technology to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above description, but instead should be determined with reference to the appended claims along with their full scope of equivalents.

What is claimed is:

1. A method for detecting a parameter of at least one gas comprising:
    receiving the at least one gas at a gas sensor included in a first device;
    measuring a density of the at least one gas;
    at least one of a) heating and b) cooling the at least one gas with a first thermal input; determining a first rate at which the at least one gas changes temperature when at least one of heating and b) cooling the at least one gas;
    comparing at least one of the density and the first rate to a reference database of gases; determining at least one of a) a category b) a lower explosive limit and c) a concentration of the at least one gas; and
    generating at least one output signal reflective of at least one of a) a category b) a lower explosive limit and c) a concentration of the at least one gas;
    receiving the least one output signal from the gas sensor and another output signal from at least one other gas sensor, the other gas sensor being included in a second device that is physically separate from the first device, the gas sensor being on one side of a safety barrier and the at least one other gas sensor being placed on the another side of the safety barrier, the safety barrier being at least one of a fire or explosion barrier;
    aggregating the least one output signal and the another output signal by a gateway using a low-power, wide area protocol; and
    transmitting the least one output signal an the another output signal to a cloud.

2. The method of claim 1, further comprising displaying at least one of a) a category b) a lower explosive limit and c) a concentration of the at least one gas on at least a first output interface.

3. The method of claim 1, further comprising:
    both heating and cooling the at least one gas, wherein the first rate at which the at least one gas changes temperature is calculated when heating the at least one gas, and a second rate at which the at least one gas changes temperatures is calculating when cooling the gas; and
    comparing the second rate to the reference database.

4. The method of claim 3, wherein the heating and the cooling the at least one gas occurs sequentially using the gas sensor.

5. The method of claim 3, wherein the heating and the cooling the at least one gas occurs in parallel using a plurality of gas sensors that include the gas sensor.

6. The method of claim 1, further comprising calibrating the gas sensor.

7. The method of claim 1, further comprising:
    at least one of a) calculating a humidity of the at least one gas and b) calculating a pressure of the at least one gas; and
    compensating at least one of a) the density and b) the first rate for at least one of the humidity and the pressure.

8. The method of claim 1, wherein the category of the at least one gas is a function of a number of carbon atoms present in the at least one gas.

9. The method of claim 1, further comprising identifying the at least one gas.

10. The method of claim 1, further comprising receiving a plurality of gases by the gas sensor.

11. The method of claim 10, further comprising determining an aggregate lower explosion limit for the plurality of gases.

12. The method of claim 1, wherein the at least a first output interface is integrated within a handheld sensor.

13. The method of claim 1, further comprising wirelessly transmitting the at least one output signal reflective of at least one of a) a category b) a lower explosive limit and c) a concentration of the at least one gas to the at least the first output interface.

14. A gas sensor system comprising:
  an equipment;
  a lora concentrator gateway;
  a cloud service; and
  at least one gas sensor configured to receive at least one gas to be sampled, the at least one gas sensor comprising:
  a processor configured to implement computer executable instructions;
  a first output interface in communication with the processor, the first output interface including;
  a computer memory in communication with the processor and storing data representing a reference database of gases and computer executable instructions, that when implemented by the processor cause the processor to:
  measure a density of the at least one gas;
  at least one of a) heat and b) cool the at least one gas with a first thermal input;
  determine a first rate at which the at least one gas changes temperature when at least one of
  a) heat and b) cool the at least one gas;
  compare at least one of the density and the first rate to a reference database of gases; and
  determine at least one of a) a category b) a lower explosive limit and c) a concentration of the at least one gas;
  generate at least one output signal reflective of at least one of a) a category b) a lower explosive limit and c) a concentration of the at least one gas;
  display at least one of a) a category b) a lower explosive limit and c) a concentration of the at least one gas on at least the first output interface;
  transmit the at least one output signal to the cloud service through the lora concentrator gateway when the at least one gas has been determined to be explosive;
  wherein the at least one gas sensor does not require bump testing, calibration, or use of a correction factor; and
  wherein the cloud service is configured to transmit an actuation signal to the equipment to perform an action of closing a valve in response to the least one output signal, the equipment being configured to receive the actuation signal and close the valve in response.

15. The gas sensor system of claim 14, wherein the at least one gas sensor is a micro-electrical mechanical system.

16. The gas sensor system of claim 14, wherein the at least one gas sensor comprises at least one micro-hotplate.

17. The gas sensor system of claim 14, wherein the processor is further configured to:
  both heat and cool the at least one gas, wherein the first rate at which the at least one gas changes temperature is calculated when the at least one gas is heated, and a second rate at which the at least one gas change temperatures is calculating when cooling the gas; and
  compare the second rate to the reference database.

18. The gas sensor system of claim 14, wherein the at least one gas sensor, the processor, the at least one output interface, and the computer memory are packaged within a node, and wherein the at least one output interface is wirelessly coupled to the node, are packaged within a handheld shell.

19. The gas sensor system of claim 14, further comprising at least one of a) wireless communication component and b) a wired communication component.

20. The gas sensor system of claim 14, further comprising at least one of a positioning system, an accelerometer, a power supply, a humidity sensor, and a pressure sensor, wherein the positioning system further comprises at least one global positioning system receiver coupled to the processor.

* * * * *